United States Patent [19]

Moldowan et al.

[11] Patent Number: 4,496,548

[45] Date of Patent: Jan. 29, 1985

[54] COMPOSITION AND METHOD FOR REDUCING HANGOVER

[76] Inventors: Mervin J. Moldowan; Carol Moldowan, both of 480 Benton View Dr., Philomath, Oreg. 97370

[21] Appl. No.: 463,736

[22] Filed: Feb. 4, 1983

[51] Int. Cl.³ .................. A61K 31/70; C07H 17/04
[52] U.S. Cl. .................................... 514/27; 536/8
[58] Field of Search ....................... 424/180; 536/8

[56] References Cited

U.S. PATENT DOCUMENTS 2,962,515 11/1960 Diezfalusy et al. .............. 536/8
3,084,154 4/1963 Sakieki et al. .................. 536/8
3,346,559 10/1967 Klosa ............................... 536/8
3,953,423 4/1976 Hadhanyi ........................ 536/8

Primary Examiner—Johnnie R. Brown
Attorney, Agent, or Firm—Chernoff, Vilhauer, McClung, Birdwell & Stenzel

[57] ABSTRACT

A novel composition and method is disclosed for preventing hangover effects in humans caused by consumption of alcoholic beverages. The composition comprises thiamine, ascorbic acid, at least one of cystein or cysteic acid, and at least one flavonoid or flavonoid complex selected from hesperidin, rutin, and hesperidin-methyl-chalcone. Preferred administration is orally, before consumption of alcohol.

7 Claims, No Drawings

COMPOSITION AND METHOD FOR REDUCING HANGOVER

BACKGROUND OF THE INVENTION

It has frequently been observed that consumption of alcoholic beverages gives rise to the discomfort known as "hangover." Hangover effects are experienced as unpleasant, and seem to vary in intensity and symptoms according to the individual. The most common hangover effects experienced are fatigue, headache, dizziness, nausea, thirst, tension, anxiety, paleness, tremor, perspiration, halitosis and nystagmus. Prevention of some or all of these effects would be desirable not only from the individual sufferer's standpoint, but also from the viewpoint of employers and society in general, since much productive time is lost by individuals suffering therefrom.

The pathogenesis of hangover effects following consumption of alcohol is not precisely known. Some experiments indicate that these effects can be caused by the ethyl alcohol in the blood, by the congeners present in the beverage containing ethyl alcohol, or by a combination of both. Other experiments have indicated that hangover effects begin to appear with declining blood alcohol. In any case, as is well known, the symptoms appear after cessation of alcohol consumption.

Thiamine hydrochloride has been included in one part of a two-part composition for hangover relief, the composition also containing an analgesic, an antidepressant, an antacid and other ingredients as disclosed in Rice U.S. Pat. No. 3,829,569. Citric acid in the form of sodium citrate in solution and in combination with aspirin is also known to relieve hangover symptoms. Ascorbic acid has also been reported to reduce headache induced by the interaction of disulfiram and ethanol. However, the type of headache induced by the disulfiram and ethanol interaction is not similar to that produced by ethanol alone, since the symptoms of the former begin almost immediately following ethanol administration to disulfiram-treated patients whereas in the case of headache following ingestion of ethanol alone, they do not appear until eight to twelve hours later.

While a number of over-the-counter products are available for the relief of hangover, very few are useful for the prevention thereof. In fact, some of the more commonly used drugs, such as compositions containing aspirin, should not be used prior to ethanol consumption since their toxic effects are intensified thereby.

SUMMARY OF THE INVENTION

The present invention comprises a novel composition and method for preventing or reducing the effects of hangover. The composition comprises thiamine, ascorbic acid, at least one of cysteine or cysteic acid, and at least one flavonoid or flavonoid complex selected from hesperidin, rutin, or hesperidin-methyl-chalcone. Relief is afforded by ingestion of the composition of the present invention before, during or after consumption of ethyl alcohol. The present invention is especially suitable for prevention of hangover by administration before alcohol consumption.

DETAILED DESCRIPTION OF THE INVENTION

The novel composition of the present invention comprises essentially four types of ingredients: thiamine, ascorbic acid, at least one of cystein or cysteic acid, and at least one of a flavonoid or flavonoid complex selected from hesperidin, rutin, or hesperidin-methylchalcone.

The composition may be administered before, during or after alcoholic consumption and when administered before is effective in prevention of hangover symptoms. Administration may take place by any known conventional method, but the preferred method is by oral ingestion in powdered or tablet form.

Thiamine may be present in any of its known forms that are not toxic to man, including its mono-, di- and triphophoric acid salts and esters, hydrochloride and mononitrate in an amount of from 5 to 70% by weight, preferably 23%. Ascorbic acid or vitamin C may be of a synthetic or natural origin and may be present in an amount from 12 to 80% by weight, preferably 47%. The third component, cysteine or cysteic acid, may be present from 0 to 90% by weight, preferably 5%. The last type of ingredient, a flavonoid or flavonoid complex may be present in an amount from about 1.5 to about 85% by weight, preferably 23%. More than one flavonoid may be present to make up the preferred weight percentage. The flavonoids may be synthetic or from natural sources and may be substantially pure, as in the case of rutin, hesperidin and hesperidin-methyl-chalcone, or contaminated with noninterferring organic impurities such as flavonoid complexes obtained from fruit or vegetable extracts.

EXAMPLES

EXAMPLE 1

Seven subjects who had consumed 120 ml ethanol in the form of whiskey and beer (type or types of alcoholic beverages, e.g., white wine, bourbon, etc.) over a period of 5 hours, suffered severe hangover symptoms 8–12 hours later, including headache, nausea, halitosis, fatigue, and tremor.

The same group ingested the composition shown below immediately prior to consumption of the same amounts of the same alcoholic beverages over the same time period as in Example 1, but suffered either no hangover symptoms at all or substantially reduced symptoms:

Thiamine hydrochloride 100 mg
Ascorbic acid 200 mg
Cysteine 20 mg
Hesperidin 100 mg The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A composition for reducing effects associated with the consumption of ethyl alcohol by humans comprising:
   (a) 12% to 80% by weight ascorbic acid;
   (b) 5% to 70% by weight thiamine;
   (c) 10% to 90% by weight of a compound selected from cysteine and cysteic acid; and
   (d) 1.5% to 85% by weight of a flavonoid or flavonoid complex selected from the group consisting essentially of rutin, hesperidin, and hesperidin-methyl-chalcone.

2. The composition of claim 1 wherein ascorbic acid is present in an amount of from about 100 mg to about 5 grams, thiamine is present in an amount of from about 5 mg to about 1 gram, cysteine or cysteic acid is present in an amount of from about 10 mg to about 2 grams, and said flavonoid is present in an amount of from about 10 mg to about 1 gram.

3. A method for reducing effects associated with the consumption of ethyl alcohol by humans, which comprises ingestion prior to, during, or immediately following consumption of ethyl alcohol, an effective amount of a composition comprising:
  (a) 12% to 80% by weight ascorbic acid;
  (b) 5% to 70% by weight thiamine;
  (c) 10% to 90% by weight of a compound selected from cysteine and cysteic acid; and
  (d) 1.5% to 85% by weight of a flavonoid or flavonoid complex selected from the group consisting essentially of rutin, hesperidin, and hesperidin-methyl-chalcone.

4. The method of claim 3 wherein said composition is ingested orally.

5. The method of claim 4 wherein said composition is ingested in the form of tablets.

6. The composition of claim 1 comprising 47% by weight ascorbic acid, 23% by weight thiamine, 5% by weight cysteine or cysteic acid, and 23% by weight of a flavonoid or flavonoid complex.

7. The method of claim 3 wherein said composition comprises 47% by weight ascorbic acid, 23% by weight thiamine, 5% by weight cysteine or cysteic acid, and 23% by weight of a flavonoid or flavonoid complex.

* * * * *